United States Patent [19]
Faber et al.

[11] Patent Number: 6,029,507
[45] Date of Patent: Feb. 29, 2000

[54] METHOD AND EQUIPMENT FOR THE CHARACTERIZATION OF SUSPENSIONS

[75] Inventors: Gerard Faber, Delfgauw; Hugo Cornelis Lucas Vos, Bergschenhoek; Mathilde Gertrudis Maria De Kroon, Delft, all of Netherlands

[73] Assignee: Nederlandse Organisatie voor Toegepast Natuurwetenschappelijk Onderzoek TNO, Netherlands

[21] Appl. No.: 08/834,049

[22] Filed: Apr. 10, 1997

[30] Foreign Application Priority Data

Apr. 10, 1996 [NL] Netherlands ............................ 1002836
Jul. 15, 1996 [NL] Netherlands ............................ 1003595

[51] Int. Cl.$^7$ .................................................. G01N 15/06
[52] U.S. Cl. ........................... 73/61.75; 73/600; 73/614; 73/602; 73/865.5
[58] Field of Search ................................ 73/61.75, 64.53, 73/865.5, 866, 597, 629, 599, 602, 600, 614

[56] References Cited

U.S. PATENT DOCUMENTS

| 3,269,172 | 8/1966 | McGaughey ............................ 73/61.75 |
| 3,946,600 | 3/1976 | Rettig et al. . | |
| 4,240,287 | 12/1980 | Mast et al. .............................. 73/61.75 |
| 4,381,674 | 5/1983 | Abts ....................................... 73/61.75 |

FOREIGN PATENT DOCUMENTS 1012010  12/1965  United Kingdom .

OTHER PUBLICATIONS

Journal of the Acoustical Society of America, entitled Application of 30MHZ Acoustic Scattering to the Study of Human Red Blood Cells, By M. S. Roos et al., Apr. 1988.

Journal of the Acoustical Society of America, entitled Quantitative Grain Size Evaluation Using Ultrasound Backscattered Echoes, By Saniie et al.

*Primary Examiner*—Hezron Williams
*Assistant Examiner*—Nashmiya Fayyaz
*Attorney, Agent, or Firm*—Bachman & LaPointe, P.C.

[57] ABSTRACT

Method and equipment for the detection and identification of particles in a suspension with the aid of acoustic signals, directed at at least one measurement volume within the suspension, via reception of acoustic reflection signals, conversion of the acoustic reflection signals into electrical reflection signals, counting the number of electrical reflection signals which have an amplitude in excess of a predetermined value and converting the count into numbers of particles which are larger than a certain size, at least one curve being composed on the basis of a cumulative count of the number of reflection signals which have an amplitude in excess of a specific value as a function of the amplitude and the at least one curve being compared with predetermined standard cumulative count curves and material properties, particle concentration, particle size distribution and/or particle characteristics, such as particle shape, particle size and standard deviation thereof, are deduced from the comparison.

16 Claims, 11 Drawing Sheets

$C = 9.10^9 \text{ m}^{-3}$;

$\sigma_D = 1 \text{ }\mu\text{m}$;

1: $\mu_D = 15 \text{ }\mu\text{m}$;

2: $\mu_D = 16 \text{ }\mu\text{m}$;

3: $\mu_D = 17 \text{ }\mu\text{m}$;

4: $\mu_D = 18 \text{ }\mu\text{m}$;

5: $\mu_D = 19 \text{ }\mu\text{m}$;

6: $\mu_D = 20 \text{ }\mu\text{m}$;

$C = 9.10^9 \text{ m}^{-3}$;

$\mu_D = 15 \text{ }\mu\text{m}$;

7: $\sigma_D = 0.5 \text{ }\mu\text{m}$;

8: $\sigma_D = 1.0 \text{ }\mu\text{m}$;

9: $\sigma_D = 1.5 \text{ }\mu\text{m}$;

10: $\sigma_D = 2.0 \text{ }\mu\text{m}$;

11: $\sigma_D = 2.5 \text{ }\mu\text{m}$;

$\mu_D = 15 \; \mu m;$ $\sigma_D = 1 \; \mu m;$

12: $C=5.10^9 \, m^{-3}$

13: $C=7.10^9 \, m^{-3}$

14: $C=9.10^9 \, m^{-3}$

15: $C=11.10^9 \, m^{-3}$

16: real distribution ( ——— )

17: inversion result with Singular Value Decomposition (o)

18: Inversion result with stochastic approach (+)

19: real distribution ( —— )

20: inversion result with stochastic approach (+)

METHOD AND EQUIPMENT FOR THE CHARACTERIZATION OF SUSPENSIONS

BACKGROUND OF THE INVENTION

The present invention relates to a method for the detection and identification of particles in a suspension, comprising the following steps:

a. generation of acoustic signals having the form of a beam using an acoustic source;

b. directing the acoustic signals at at least one measurement volume within the suspension, the boundaries of the measurement volume in the axial direction with respect to the acoustic source being defined with the aid of time windows;

c. reception of acoustic reflection signals produced by reflection of the acoustic signals by the particles in the at least one measurement volume;

d. conversion of the acoustic reflection signals into electrical reflection signals;

e. counting numbers of electrical reflection signals which have an amplitude in excess of a predetermined value and conversion thereof into numbers of particles which are larger than a certain size.

A method of this type is disclosed in British Patent 1,012,010, which describes a method and equipment for counting and measuring such particles, wherein acoustic samples are taken in various measurement volumes along the acoustic axis of the acoustic transducer in the suspension. By using suitable time windows when receiving reflected acoustic signals, the particles in, for example, four predetermined measurement volumes, which are each located a predetermined distance away from the transducer, are counted. By making use of a threshold voltage which the electrical signals produced from the acoustic signals must exceed in order to be counted, which threshold voltage is different for each zone, a minimum size for the particles to be counted is selected for each zone. Assuming that the particle distribution is the same in each zone, a rough estimate of the number of particles, subdivided according to particle size, can be obtained using this known method and using simple mathematical methods.

U.S. Pat. No. 3,774,717 describes a method and equipment for the detection and identification of small particles, for example biological cells, which, for example, are located in a medium which flows transversely to the direction of propagation of an acoustic signal. Each of the particles gives a specific scatter of the acoustic signal, depending on the size, the shape and the acoustic impedance of the particles. The acoustic signal has a wavelength and an effective cross-section of the order of magnitude of the particles to be detected and identified. Blood cells, for example, are detected with the aid of an acoustic signal of 860 MHz. Therefore, particles can be identified with the aid of techniques which are known from radar technology. The technique disclosed in this patent is unsuitable for in vivo detection and identification because the wavelengths used allow only very restricted depths of penetration in biological tissue.

The methods described above are based on the ultrasonic pulse-echo technique. With this technique use can be made of a so-called ultrasonic transducer, which converts an applied electrical pulse into an acoustic (ultrasonic) signal and which is also capable of converting an acoustic (ultrasonic) signal which is incident on the reception surface back into an electrical signal. Therefore, the transducer serves as transmitter and as receiver for ultrasonic signals. It is also possible to use independent transmitters and receivers. A high-frequency pulse-echo recording of the flowing suspension is made. A focusing transducer can be used for this. In FIG. 1 the "illuminating" sound signal is shown diagrammatically in an arrangement known per se.

As is shown in FIG. 1, the principal axis z of the sound beam 20 generated by a transducer 23 is perpendicular to the direction of flow P of the suspension 21 flowing in a channel 24 and, consequently, to the direction of movement of the particles 22 present in the suspension. When a particle 22 passes through the sound beam 20, the incident sound field will be reflected by the particle and the reflected signal will be captured by the transducer 23. The received signal is converted by the transducer 23 into an electrical signal, which is transmitted to the transmission and reception electronics 25. The transmission and reception electronics 25 transmit the signal to a computer 26, which is connected to a memory 27 for storing measurement data. The computer 26 is provided with suitable software for evaluation of the measurement data. The electrical signal from a single measurement is indicated diagrammatically by s and is a time signal, the time axis t indicating the propagation time of the sound. The response of the particle 22 in the measurement volume can be detected in the recording at that moment in time which corresponds to the propagation time of the ultrasonic pulse between transducer 23 and reflecting particle 22 and back again.

Only reflections within an applied time window $[t_1, t_2]$ (see FIG. 1) are processed in the analysis. The measurement volume is thus limited in the axial direction by $z_1 = t_1 \cdot c/2$ and $z_2 = t_2 \cdot c/2$ (c is the speed of propagation of the sound). In the lateral direction the measurement volume is limited by the shape of the acoustic beam.

A method for counting the number of particles using a measurement set-up of this type is described in the above-mentioned patents and in Croetsch, J. G.; "Theory and application of acoustic particle monitoring systems", Jr. Advances in Instrumentation and Control 45 (1990), Part 1. Generally speaking, with this method a specific threshold value is chosen for the amplitude of the reflected signal. If the recorded signal within the time window $[t_1, t_2]$ is in excess of this threshold value, this is interpreted as the presence of a particle in the measurement volume. On condition that the particle concentration is so low that the risk of the simultaneous presence of more than one particle within the measurement volume is negligible, the particle concentration can be estimated by counting the number of recordings in excess of the set threshold value.

This method takes no account of variations in particle size and no distinction is made between different types of particles which are possibly present in the suspension.

SUMMARY OF THE INVENTION

The aim of the present invention is to provide a reliable and more precise method for the characterisation of a suspension and the particles present in the suspension. In this context characterisation is understood to be estimation of the particle concentration, the particle size distribution, the shape of the particles and the reflectivity of the particles.

A further aim of the invention is to provide a method for the characterisation of suspensions and the particles contained therein, with which method account does not necessarily have to be taken of the condition that no more than one particle may be present in the measurement volume at any one time.

The first-mentioned objective is achieved with a method of the above-mentioned type, which method is characterized by the following steps:

f. composing at least one curve on the basis of a cumulative count of the number of reflection signals which have an amplitude in excess of a specific value as a function of the amplitude;

g. comparison of the at least one curve with predetermined standard cumulative count curves and deduction of at least one feature from a set of features comprising: material properties, particle concentration, particle shapes, particle size and standard deviation thereof and particle size distribution.

Material properties thus deduced may, e.g. be density and compressibility.

A method of this type can be used successfully where the suspension flows relative to the acoustic source, where the acoustic source is moved relative to the suspension (for example along the suspension), where, for whatever reason, the properties of the suspension change as a function of time and the acoustic source is fixed, and where an array of acoustic sources is used instead of a single acoustic source, the acoustic sources always being activated in succession.

For the purposes of the further objective, one embodiment of the method according to the invention is characterized in that:

in step a, the acoustic beam generated has such a large aperture, and the time which elapses between two successive measurements is so short, that each particle is exposed several times while passing through the beam and that, depending on the lateral position of a particle in the measurement volume, a varying angle-dependent reflection of the acoustic signal is produced;

prior to step f, one or more different types of particles present in the suspension are identified on the basis of a series of angle-dependent reflection signals received successively over time;

when composing the curve in step f, the maximum value of the amplitudes of a series of successive angle-dependent reflection signals, received over time, from a detected particle from the one or more groups is taken as the amplitude of the electrical signals, which are produced after conversion of the acoustic reflection signals from that particle.

With a method of this type, the measurement volume chosen is so large that, within the measurement volume, the angle of incidence varies as a function of the lateral position. If a particle in the flowing suspension is "exposed" various times in succession by an acoustic signal in pulse form, the successive reflection signals differ as a consequence of angle-dependent reflection. The angle-dependent behaviour is highly dependent on the shape of the particle, as can be seen from, inter alia: M. G. M. de Kroon: "Acoustic backscatter in arteries—Measurements and modelling of arterial wall and blood", thesis 1993, ISBN 90-9006182, Section II. Therefore, a particle can be characterized by this means.

In an alternative embodiment the present invention relates to a method for the detection and identification of particles in a suspension, comprising the following steps:

a. generation of acoustic signals using an acoustic source;

b. directing the acoustic signals at at least one measurement volume within the suspension, the boundaries of the measurement volume in the axial direction with respect to the acoustic source being defined with the aid of time windows;

c. reception of acoustic reflection signals produced by reflection of the acoustic signals by the particles in the at least one measurement volume;

d. conversion of the acoustic reflection signals into electrical reflection signals;

e. counting numbers of electrical reflection signals which have an amplitude in excess of a predetermined value and conversion thereof into numbers of particles which are larger than a certain size;

wherein the method also comprises the step of applying an inversion algorithm on the amplitudes of the electrical reflection signals to deduce at least one feature from a set of features comprising: material properties, particle concentration, particle shapes, particle size and standard deviation thereof and particle size distribution.

The present invention also relates to equipment for the detection and identification of particles in a suspension, comprising:

a. an acoustic source for the generation of acoustic signals in pulse form;

b. means for directing the acoustic signals at at least one measurement volume within the suspension, the boundaries of the measurement volume in the axial direction with respect to the acoustic source being defined with the aid of time windows;

c. means for receiving acoustic reflection signals produced by reflection of the acoustic signals by the particles in the at least one measurement volume;

d. means for converting the acoustic reflection signals into electrical reflection signals;

e. means for counting numbers of electrical reflection signals which have an amplitude in excess of a predetermined value and for converting the count into numbers of particles which are larger than a certain size;

wherein the equipment also comprises:

f. means for composing at least one curve on the basis of a cumulative count of the number of reflection signals which have an amplitude in excess of a specific value as a function of the amplitude;

g. means for comparing the at least one curve with predetermined standard cumulative count curves and for deducing at least one feature from a set of features comprising: material properties, particle concentration, particle shapes, particle size and standard deviation thereof and particle size distribution.

In one embodiment, such equipment is characterized in that during operation, the acoustic source generates an acoustic beam which has such a large aperture, and makes the time which elapses between two successive measurements so short, that each particle is exposed several times while passing through the beam and that, depending on the lateral position of the particles in the measurement volume, a different angle-dependent reflection of the acoustic signal is produced;

identification means are also present for identification of one or more different groups of particles present in the suspension on the basis of a series of successive angle-dependent reflection signals received over time;

the means for composing the cumulative curve compose the curve, the maximum value of the amplitudes of a series of successive angle-dependent reflection signals, received over time, from a detected particle being taken as the amplitude of the electrical signals, which are produced after conversion of the acoustic reflection signals from that particle.

In the last-mentioned equipment, use is advantageously made of the angle-dependent reflection behaviour of acoustic signals reflected by particles and it is no longer necessary to meet the condition that only one particle may be present in the measurement volume at any one time, as has been explained above.

In an alternative embodiment the invention relates to equipment for the detection and identification of particles in a suspension, comprising:

- a. an acoustic source for the generation of acoustic signals;
- b. means for directing the acoustic signals at at least one measurement volume within the flowing suspension, the boundaries of the measurement volume in the axial direction with respect to the acoustic source being defined with the aid of time windows;
- c. means for receiving acoustic reflection signals produced by reflection of the acoustic signals by the particles in the at least one measurement volume;
- d. means for converting the acoustic reflection signals into electrical reflection signals;
- e. means for counting numbers of electrical reflection signals which have an amplitude in excess of a predetermined value and for converting the count into numbers of particles which are larger than a certain size;

characterized in that the equipment also comprises:

- f. means for applying an inversion algorithm on the amplitudes of the electrical reflection signals to deduce at least one feature from a set of features comprising: material properties, particle concentration, particle shapes, particle size and standard deviation thereof and particle size distribution.

BRIEF DESCRIPTION OF THE DRAWINGS

The invention will be explained in more detail below with reference to a few drawings and illustrative embodiments, which are intended solely for the purposes of illustration and not as a limitation of the inventive concept.

In the drawings.

DETAILED DESCRIPTION OF THE EMBODIMENTS

Figure 1:
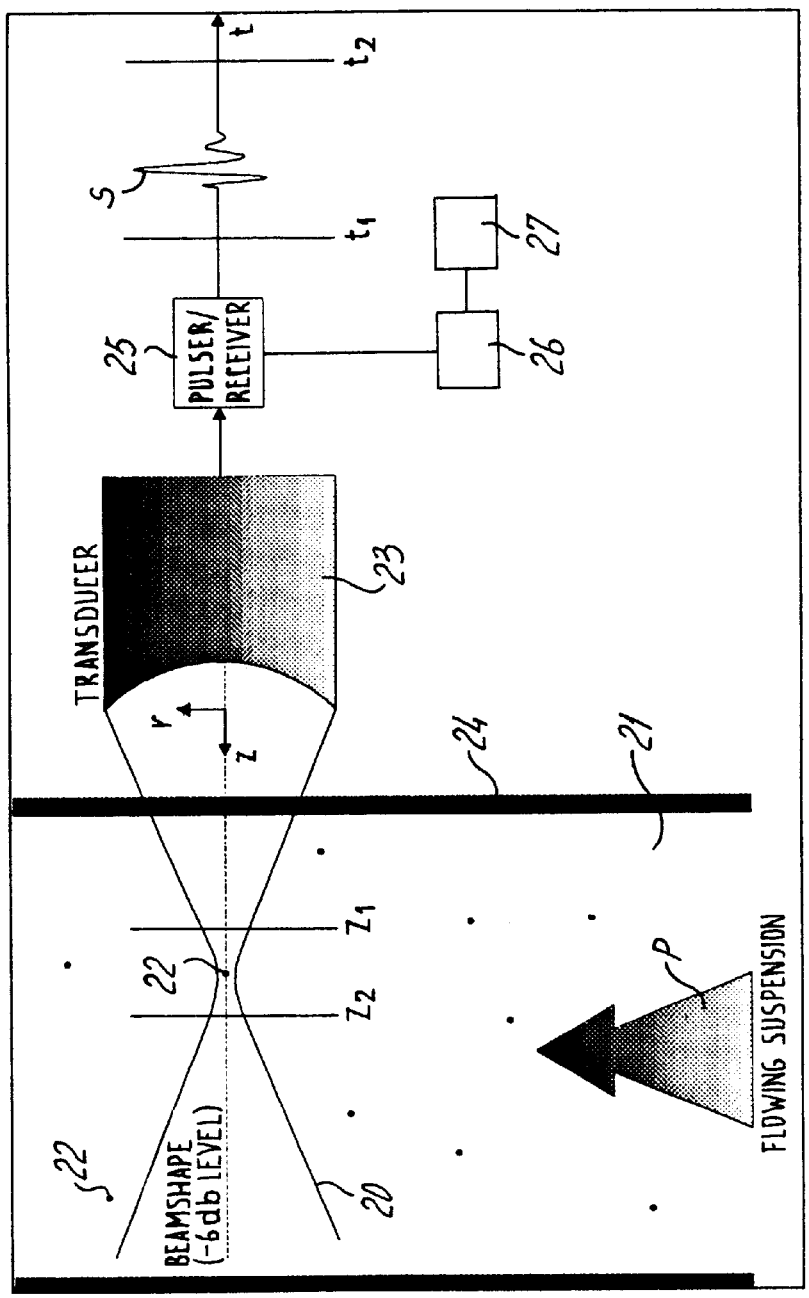
FIG. 1 shows a diagrammatic measurement set-up for the determination of the particle concentration and particle size distribution in a flowing suspension containing equivalent particles.

First of all a method for the determination of the particle size distribution and particle concentration in a suspension containing equivalent particles will be explained. Equivalent particles are understood to be particles of the same material and of the same shape, whilst the size of the particles may vary.

Not only is the number of recordings above the threshold value determined, but a complete histogram of recorded amplitudes is made. The histogram is then converted to give a cumulative count $N_c$ with the highest recorded amplitude as the start value. The cumulative count $N_c(A)$ is defined as the number of recordings with an amplitude greater than or equal to A. The cumulative count curve is simple to calculate from the histogram. The particle concentration and the particle size distribution in a suspension containing equivalent particles can be estimated from the histogram or from the count curve.

Cumulative count curves for suspensions containing equivalent particles can be simulated on the basis of the model given below.

First of all it has to be checked whether the assumption that the likelihood of finding two or more particles is negligibly small is realistic.

The Poisson distribution can be used for the probability density function f(m) for finding m particles in the measurement volume:

$$f(m) = \frac{\beta^m e^{-\beta}}{m!} \quad (1)$$

In this equation $\beta$ is the expectation value for the number of particles in the measurement volume. For suspensions with low particle concentrations and for a sufficiently small measurement volume, the likelihood of two particles being present in the measurement volume at the same time is negligibly small. In this case it can be deduced from equation (1) that the following approximation applies for the likelihood of the presence of no particles (f(0)) and of one particle (f(1)), respectively:

$$f(0) = e^{-\beta}$$
$$f(1) = 1 - e^{-\beta} \quad (2)$$

The likelihood of finding a particle can also be calculated as follows:

$$f(1) = V_{meas} C \quad (3)$$

where $V_{meas}$ is the measurement volume and C the number of particles per unit volume.

Equating f(1) from equations (2) and (3) gives an estimate for $\beta$:$S_\beta$ $$S_\beta = -\ln(1 - V_{meas} C) \quad (4)$$

Using this equation it is then possible, with the aid of equation (1), to make an estimate of the likelihood of finding two or more particles, so that it is possible to investigate whether the assumption that this likelihood is negligibly small is realistic.

The shape of the cumulative count curve depends not only on the properties of the suspension but also on the acoustic pressure distribution in the measurement volume. The probability density function for the measured amplitude for a particle of given diameter D depends on the properties of the acoustic field and will be represented by g(A|D). If the suspension consists of a collection of particles of different dimensions, the resultant cumulative count curve will be the weighted sum of the individual cumulative count curves which are associated with the particles of a constant diameter. The weighting consists in the application of the particle size distribution for the particles in the suspension concerned. The following equation then applies for the probability density function p(A) for the amplitude:

$$p(A) = \int g(A|D) h(D) d \quad (5)$$

In this equation h(D) is the probability density function for the particle diameter D.

If the measurement volume is chosen to be around the focus of the acoustic beam 20 (FIG. 1), the amplitude of the incident acoustic pressure can be approximated by a Gaussian function:

$$P(r) = P_0 e^{-\kappa r^2} \quad (6)$$

where $$\kappa = \frac{k^2}{32 f_N^2} \quad (7)$$

In this equation r is the lateral distance from the principal axis (see FIG. 1), k is the wave number and $f_N$ is the f-number of the transducer, which is defined as the quotient of the distance from the focus, $z_f$, and the transducer diameter ($f_N = z_f / 2a_t$, where $a_t$ is the radius of the transducer).

The likelihood of finding no particles, given in equation (2), indicates which fraction of the total number of measurements yields an amplitude which is less than or equal to $A_n$ (amplitude of the noise). If a particle is positioned that far form the central axis of the acoustic beam that the reflection amplitude is below the noise level $A_n$, the particle is the to be outside the measurement volume $V_{meas}$. As such the amplitude of the noise determines the lateral dimensions of the measurement volume; after all, with the aid of equation (6) it follows that:

$$R_{meas}^2 = \frac{1}{2\kappa} \ln\left(\frac{A_{max}}{A_0}\right) \quad (8)$$

$$V_{meas} = \kappa R_{meas}^2 (t_2 - t_1) + c/2 \quad (9)$$

In this equation $R_{meas}$ is the radius of the measurement volume in the lateral direction and $A_{max}$ is the maximum amplitude detected for the suspension (largest particle located on the principle axis of the beam). $V_{meas}$ is the measurement volume which is delimited in the direction of the principal axis z by the chosen time window [$t_1$, $t_2$].

For those measurements where there is a particle found in the beam, the measured amplitude will depend on the precise location of the particle concerned in the measurement volume and on the dimensions of the particle concerned.

Assuming a Gaussian acoustic beam profile in the lateral direction (Equation (6)) in the measurement volume and negligible amplitude variation in the axial direction within the selected time window, it can be deduced that the conditional probability density function g(A|D) for the measured amplitude A originating from an arbitrary particle with diameter D is given by:

$$g(A|D) = \begin{bmatrix} \frac{1}{A} \frac{1}{\ln A_0(D) - \ln A_n} & \text{if } A_n < A < A_0(D) \\ 0 & \text{if } A > A_0(D) \wedge A < A_n \end{bmatrix} \quad (10)$$

The following relationship can be derived for the conditional cumulative count G(A>A):

$$G(\underline{A} > A | D) = \begin{bmatrix} \frac{\ln A_0(D) - \ln A}{\ln A_0(D) - \ln A_n} & \text{if } A_n < A < A_0(D) \\ 1 & \text{if } A < A_n \\ 0 & \text{if } A > A_0(D) \end{bmatrix} \quad (11)$$

In these equations $A_0$ is the amplitude which would be detected from the particle concerned if the particle were located on the principal axis of the beam. The $A_0$ depends on the size of the particle. For spherical particles, the diameter of which is much smaller than the wavelength, $A_0$ is proportional to the third power of the diameter D (Rayleigh scattering):

$$A_0 = \gamma D^3 \quad (12)$$

In this equation $\gamma$ is a proportionality constant, which depends both on the transducer properties and material characteristics of the particle, like density and compressibility.

The probability density function of equation (5) is the so-called forward model of the experiment, from which the measured amplitude histogram, given the properties of the suspension (particle diameter distribution h(D)) and the properties of the acoustic field, can be calculated. This forward model needs to be inverted to be able to deduce the properties of the suspension (h(D)) from the measured amplitude. For a Gaussian pressure field, a method for inversion is described below.

The integration in equation (5) is replaced by summation and equations (10) and (12) are applied:

$$p(A_i) = \sum_j \frac{1}{A_i} \frac{1}{\ln\left(\frac{\gamma D_j^3}{A_0}\right)} h(D_j) \Delta D \quad (13)$$

where the summation is over all particle diameters $D_j$, which might give a reflection amplitude equal to $A_i$.

The likelihood for a particle to have a diameter in the interval $D_j - \Delta D/2 \ldots D_j + \Delta D/2$ is given by $h(D_j) \Delta D$, and will be denoted as $q(D_j)$. So equation (13) becomes:

$$p(A_i) = \sum_j \frac{1}{A_i} \frac{1}{\ln\left(\frac{\gamma D_j^3}{A_n}\right)} q(D_j) \qquad (14)$$

This equation can be written as a matrix product of forward matrix W with probability vector q.

$$\bar{p}(A) = W(A,D)\bar{q}(D) \qquad (15)$$

No assumptions were made about the particle diameter distribution, it was only assumed that there exists a maximum diameter, which is not a limiting restriction.

Equation (15) was deduced for a Gaussian pressure field, however, in general it is possible to deduce a matrix presentation for the relation between the particle size distribution q(D) and the amplitude distribution p(A).

There are several ways to find a (stable) pseudo-inverse of the forward matrix W which fits the parameters (i.e. the elements of vector ) to the data in a least squares sense. A standard approach for this problem is singular value decomposition (SVD).

Another, more superior method, uses a stochastic approach, which is described by Franklin (Franklin, J. N., 1970, "Well-posed stochastic extension of ill-posed linear problems", Journal of mathematical analysis and applications, vol. 31. pp 682–716 (1970). A stochastic approach means that is assumed that the parameters (q) and noise are samples drawn from random processes. The assumption yields in a smoothness constraint for the desired solution. The parameters that control the smoothness of the solution depend on the solution itself, therefore an iterative method can be used to find the optimal set of parameters.

The calculated particle size distribution, using one of above-mentioned techniques is not the true size distribution of particle in the suspension ($q_{true}$), but the apparent size distribution ($q_{app}$). This distribution deviates from the true size distribution since smaller particles cannot be detected throughout the complete measurement volume as defined by equation (9). Applying a correction factor results in the true particle size distribution of particles in the suspension. Assuming a Gaussian pressure field, the correction factor is given by:

$$q_{true}(D) = \xi q_{aDD}(D) \frac{\ln\left(\frac{A_n}{\gamma D_{max}^3}\right)}{\ln\left(\frac{A_n}{\gamma D^3}\right)} \qquad (16)$$

In this equation $D_{max}$ is the diameter of the largest particle in suspension. The factor ε is applied to normalize the area below $q_{true}$ equal to unity.

The number of measurements with an amplitude larger than $A_n$ is indicative for the number of particles C per unit volume in the suspension. Assuming a Gaussian pressure field, it can be deduced that the number of particles per unit volume is given by:

$$C = \frac{N(A > A_n)}{N_{tot} V_{meas}} \left[\frac{1}{\xi} \int_D q_{true}(D) d D\right] \qquad (17)$$

In this equation N( . . . ) gives the number of measurements for which the condition given in brackets applies. $N_{tot}$ is the total number of measurements; $V_{meas}$ is the measurement volume as defined in equation (9). The factor within straight brackets [] is a correction factor which has to be applied because smaller particles cannot be detected within the whole measurement volume.

Figure 2:
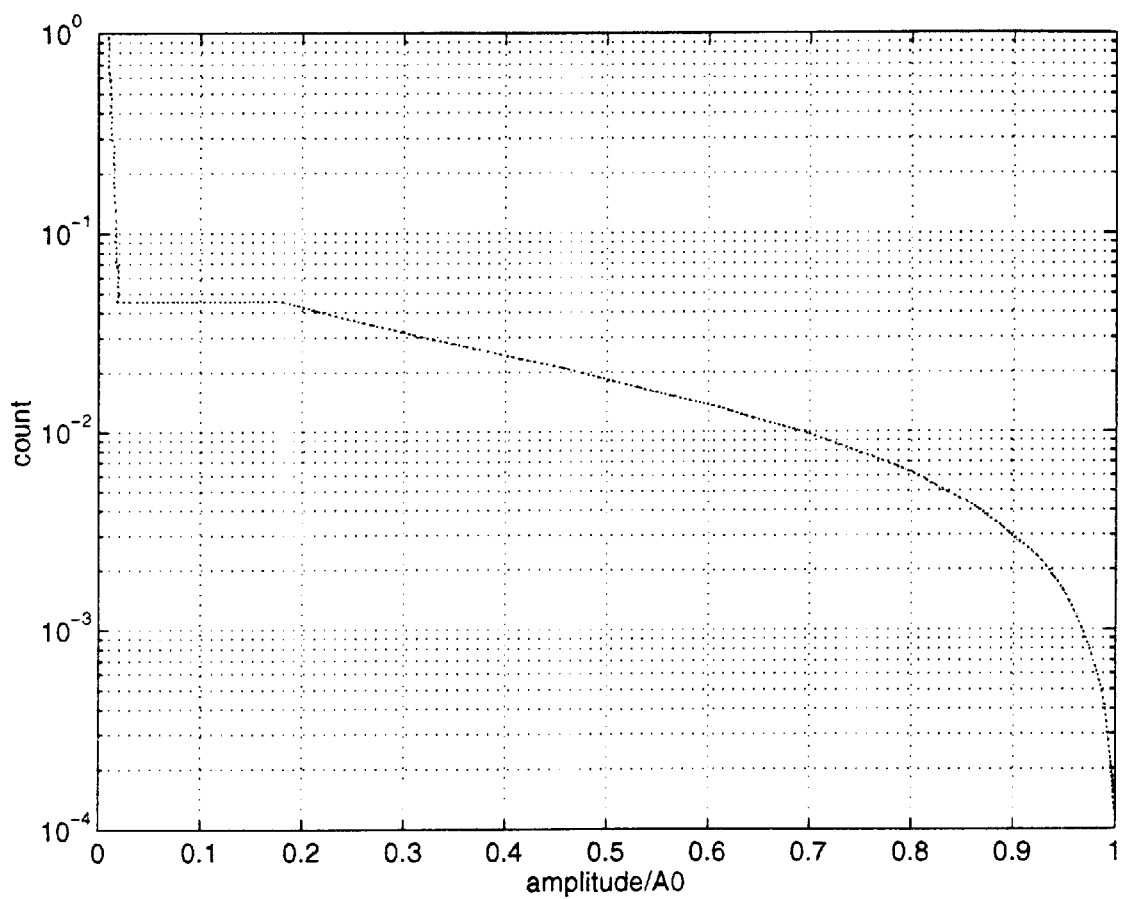
FIG. 2 shows a measured cumulative count curve for oil droplets in water (133 ppm), for an oil droplet average diameter of 40 $\mu$m.

FIG. 2 gives an example of a measured cumulative count curve for oil droplets in water (133 ppm), for an oil droplet average diameter of 40 μm.

Figure 4:
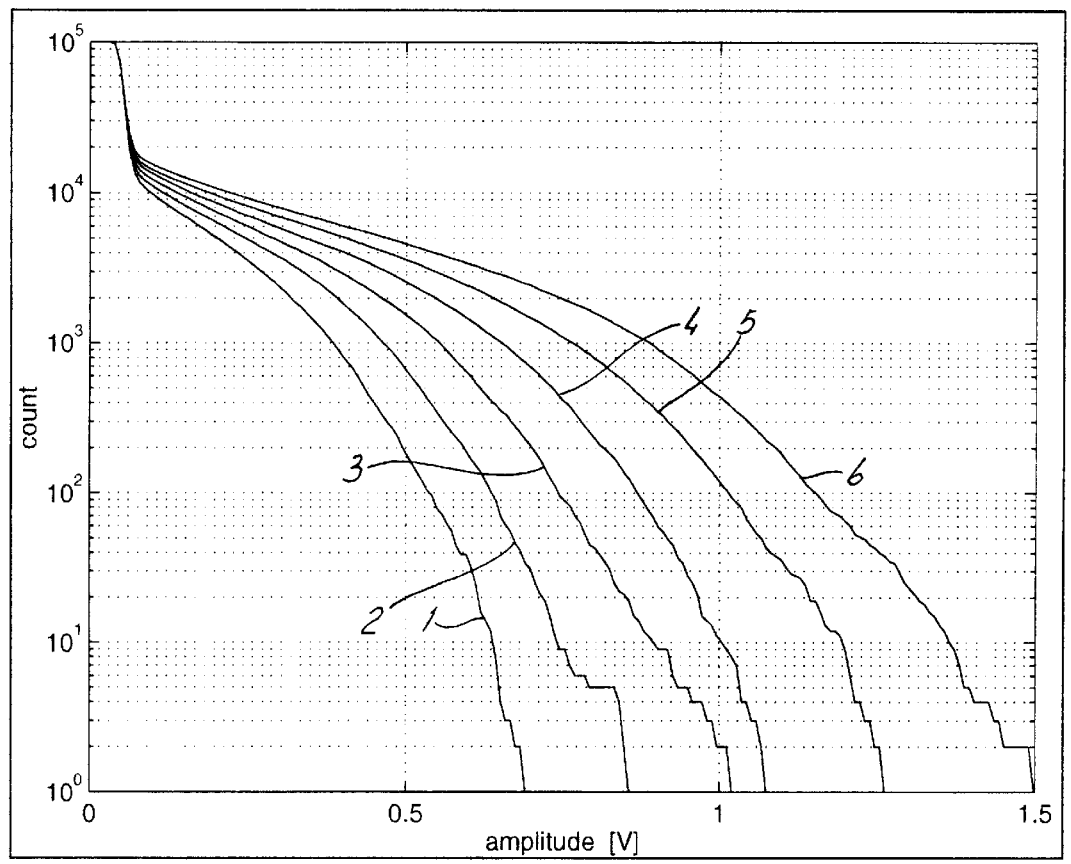
FIG. 4 shows simulated cumulative count curves for oil droplets in water, at a concentration of $9.10^9$ m$^{-3}$, for a standard deviation of the oil droplet diameters of 1 $\mu$m and an average of oil droplet diameter varying from 15 $\mu$m to 20 $\mu$m.
Figure 5:
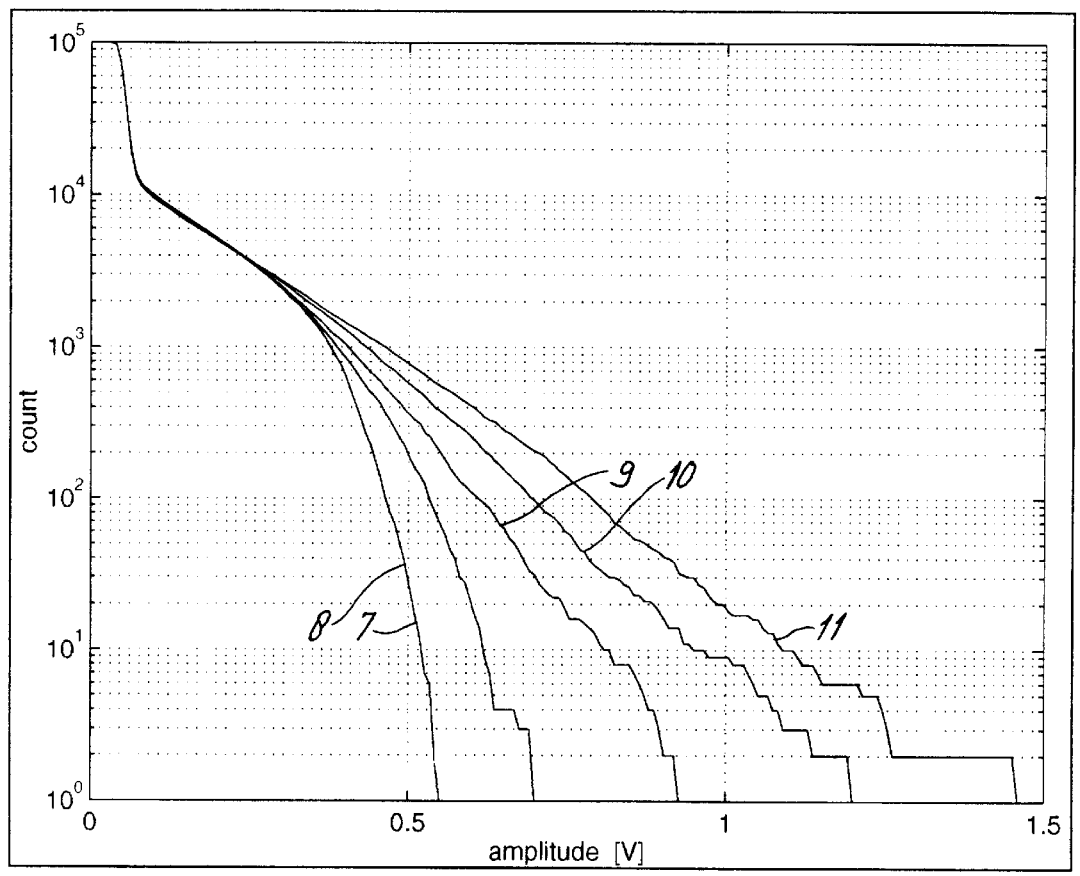
FIG. 5 shows simulated cumulative count curves for oil droplets in water, for a standard deviation of the oil droplet diameters of 1 $\mu$m and for an average of oil droplet diameter of 15 $\mu$m at a concentration varying from $5.10^9$ m$^{-3}$ to $11.10^9$ m$^{-3}$.
Figure 6:
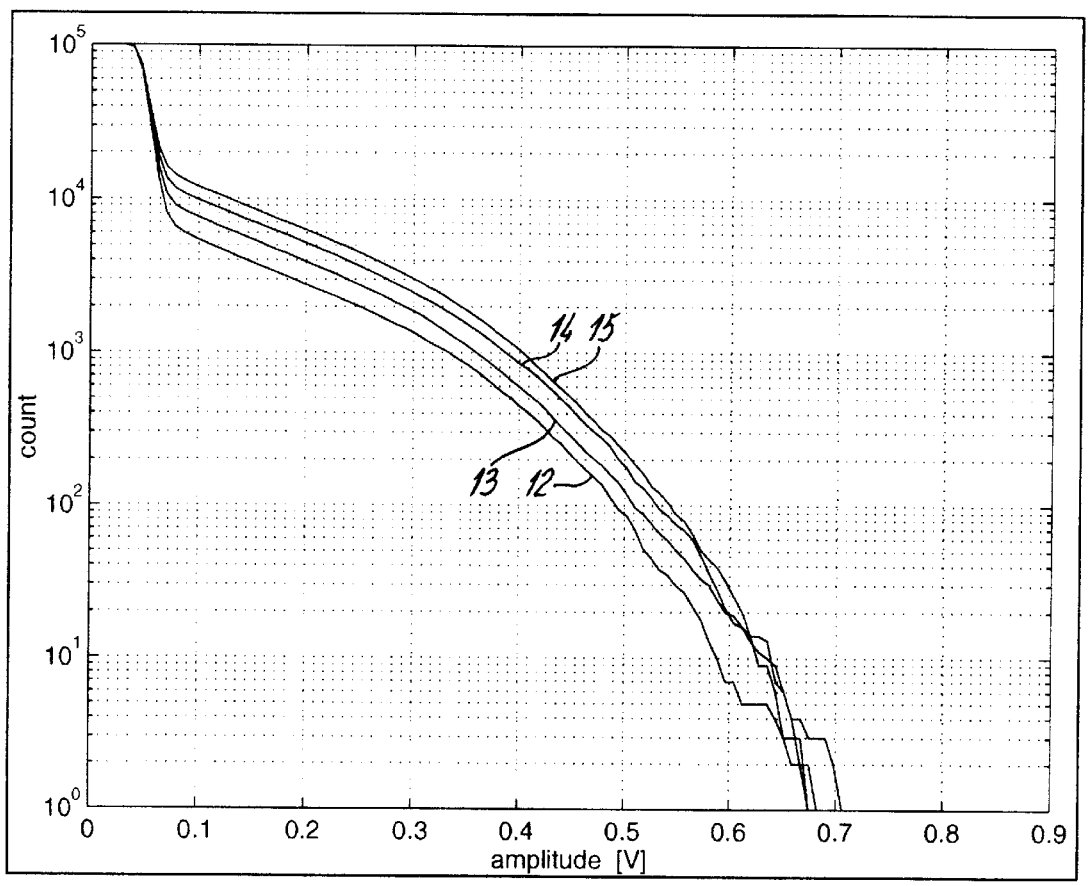
FIG. 6 shows simulated cumulative count curves for oil droplets in water, at a concentration of $9.10^9$ m$^{-3}$, for an average of oil droplet diameter of 15 $\mu$m and for a standard deviation of the oil droplet diameters varying from 0.5 to 2.5 $\mu$m.

The count curves given in FIGS. 4 to 6 are the results of simulations based on the combination of equations (5), (10) and (12).

The oil droplets are homogeneously distributed throughout the suspension. For the simulations the diameter of the droplets is normally distributed with an average of $\mu_n$ and standard deviation $\sigma_D$. The number of droplets per unit volume is C. The cumulative count curve for such a suspension depends on these three variables $\mu_D$, $\sigma_D$ and C. This is illustrated in FIGS. 4, 5 and 6, which show simulated count curves on the basis of the model described above.

Figure 3:
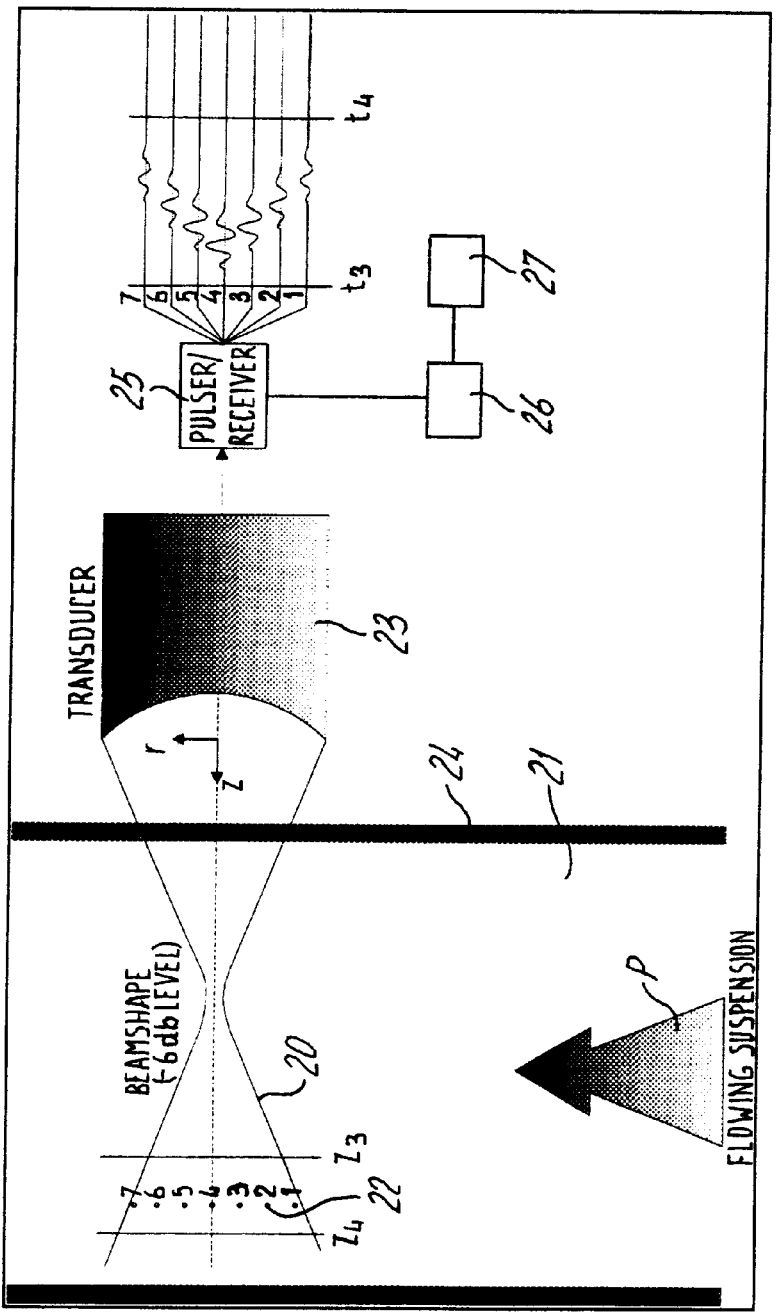
FIG. 3 shows a diagrammatic measurement set-up for the determination of the particle concentration and particle size distribution in a flowing suspension, where several particles may be present in the measurement volume.

FIG. 4 gives simulated count curves for water-oil suspension where $\mu_o$ varies between 15 and 20 μm, where $\sigma_D$ is kept constant at 1 μm and C is constant $9.10^9$ m$^{-3}$. FIG. 3 gives simulated count curves for water-oil suspension where $\sigma_D$ is varied from 0.5 to 2.5 μm, the concentration is $9.10^9$ m$^{-3}$, and the average drop diameter ($\mu_D$) is 15 μm.

Comparing FIGS. 4 and 5 show clearly that the effect of a variation in $\mu_D$ differs from the effect of a variation of $\sigma_D$. The effect of a variation in C on the cumulative count curve is illustrated in FIG. 6. In this Figure, the cumulative count curves for a concentration of $5.10^9$ m$^{-3}$, $7.10^9$ m$^{-3}$, $9.10^9$ m$^{-3}$ and $11.10^9$ m$^{-3}$, where $\mu_D$ has been kept constant at 15 μm and $\sigma_D$ has been kept constant at 1 μm, are shown. The effect of a higher C is to raise the height of the cumulative count curve for all A>$A_n$. Comparing FIG. 6 and FIG. 4 shows that the effect of a variation in C can be readily differentiated from that of a variation in $\mu_D$, whilst comparing FIG. 6 and FIG. 5 shows that the effect of C can also be readily differentiated from the effect of $\sigma_D$.

It follows from this example that the C, $\mu_D$ and $\sigma_D$ can be derived from the measured cumulative count curve for a suspension in which an unknown quantity of oil droplets of unknown $\mu_D$ and $\sigma_D$ are distributed. For this purpose measured cumulative count curves can be compared with pre-determined standard cumulative count curves for known particles. The standard cumulative count curves can, for example, be determined via simulation, as has been explained above with reference to FIGS. 4, 5 and 6. In this case, for example, a Bayesian inversion can be used to derive the particle size distribution from the cumulative count curves. As an alternative, standard cumulative count curves of this type can be determined experimentally. Standard count curves of this type can be stored in the memory 27 of computer 26, the computer 26 being equipped with suitable software for comparing measured count curves with the standard count curves. Standard methods, such as the least squares fit, can be used for this purpose. The method can, of course, also be used for suspensions containing particles which have a particle size distribution other than normal particle size distribution with characteristic values other than $\mu_D$ and $\sigma_D$.

Another method to derive C and the particle size distribution (e.g. defined by $\mu_D$ and $\sigma_D$) from a measured cumulative count curve is to apply an inversion algorithm, such like the one as given in equation (15). The capabilities of such an invention algorithm are illustrated in FIGS. 7 and 8.

Figure 7:
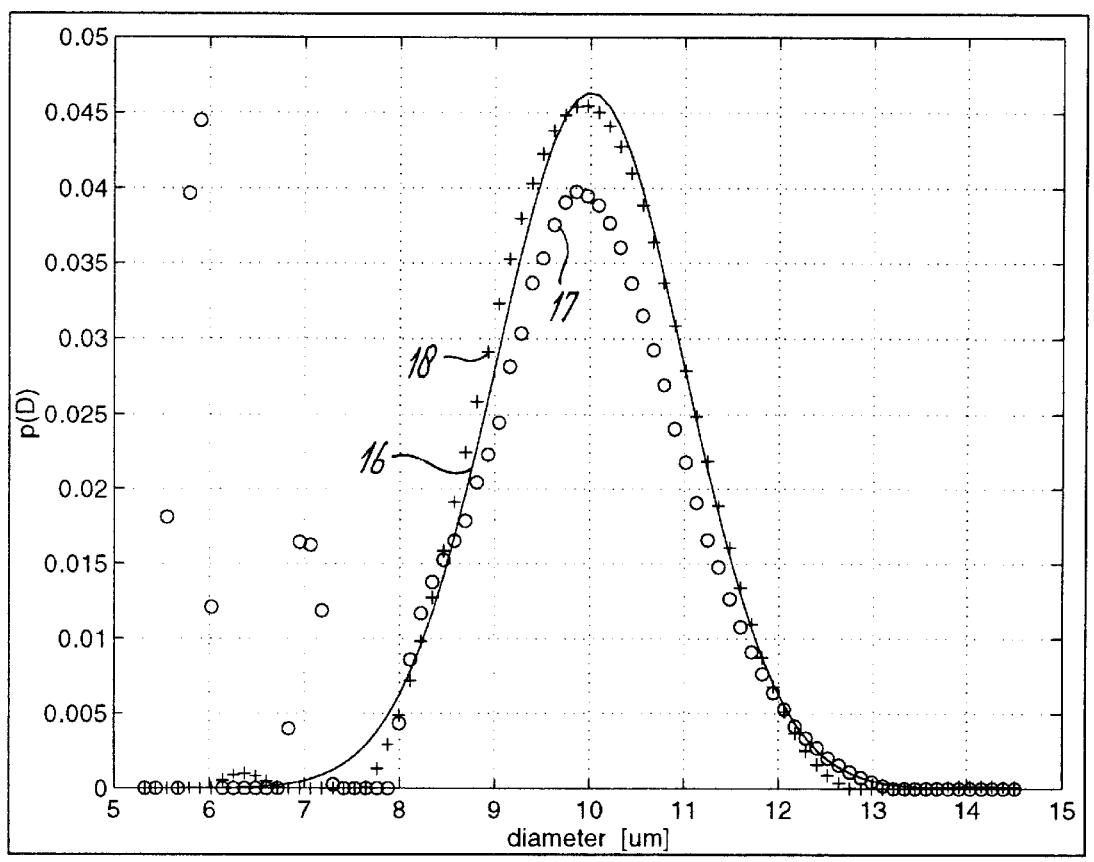
FIG. 7 shows an invention result of a inverted simulated count curve. The particle diameter is distributed according to a Gaussian distribution with an average particle diameter $\mu_D$ of 10 $\mu$m, a standard deviation $\sigma_D$ of 1 $\mu$m and the particle concentration equals $7.10^9$ m$^{-1}$.
Figure 8:
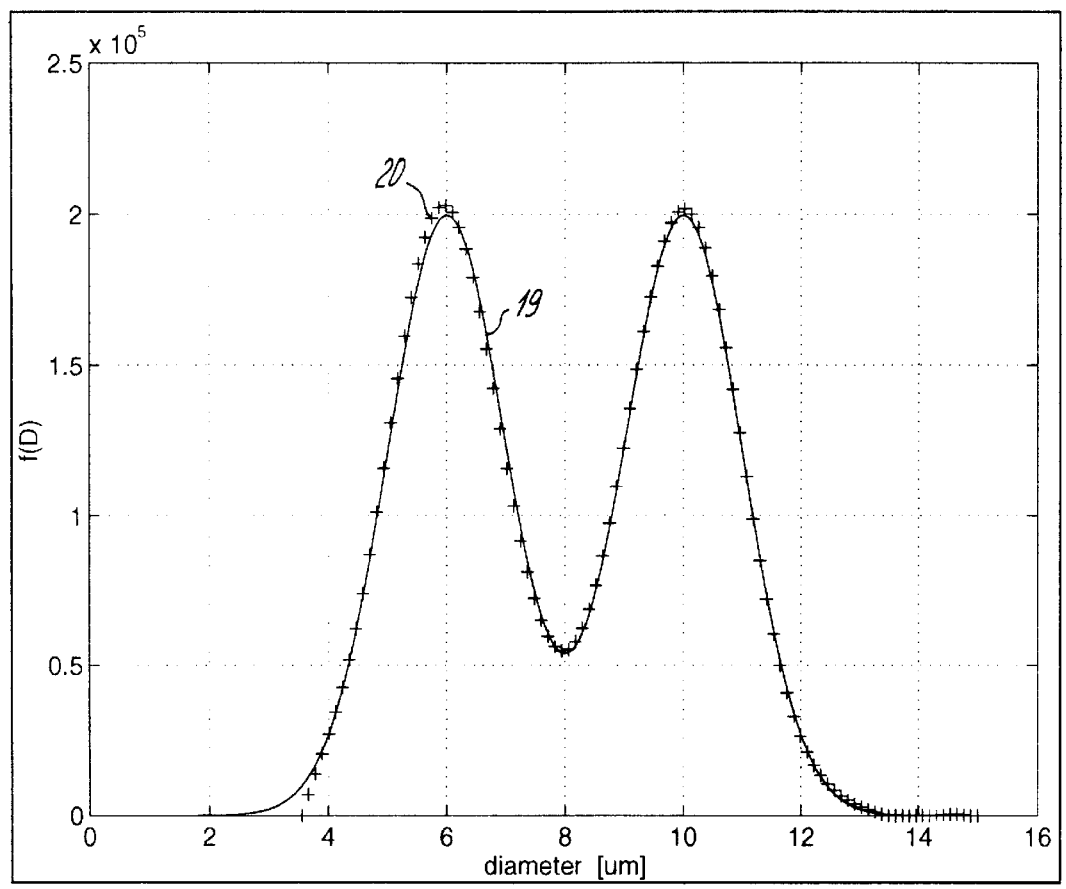
FIG. 8 shows an inversion result of a suspension with two particle components: one has a average diameter of 6 $\mu$m, the other of 10 $\mu$m.

FIG. 7 gives the inversion result using the described inversion technique given by equations (14), (15), (16). The line (curve 16) shows the exact size distribution, the circular markers (curve 17) are the result obtain using singular value decomposition and the cross markers (curve 18) are the inversion result using the stochastic approach. The Figure shows that more accurate results are obtained using the stochastic approach. To illustrate that any kind of particle size distribution can be determined using this technique, an inversion result of a non-gaussian size distribution is shown in FIG. 8. The line (curve 19) gives the exact distribution and the cross markers (curve 20) give the inversion result using the stochastic approach.

A method and set-up for the characterisation of various types of particles in a suspension will now be described.

In the above it has been assumed that there is only one type of particle in the suspension, only the size of the particles being allowed to vary. A further assumption was that the likelihood of more than one particle being present in the measurement volume at the same time is negligibly small. On these grounds, a small measurement volume in the focus region of the acoustic beam 20 was preferably chosen.

However, there are sometimes advantages in, in contrast, selecting a large measurement volume beyond the focus. This is illustrated in FIG. 3, in which the same reference numerals as in FIG. 1 refer to the same elements. The measurement volume is delimited in the axial direction of the principal axis z by $z_3$ and $z_4$ associated with time window $[t_3, t_4]$. In this case the angle of incidence within the measurement volume varies as a function of the lateral position r with respect to the principal axis z. If several reflection measurements are carried out in succession on one particle 22 while the particle is passing through the measurement volume (see FIG. 3), the angle-dependent reflection behaviour of the particle can be determined from the change in the reflection signal as a function of the lateral position. The angle-dependent behaviour is highly dependent on the shape of the particle and therefore the particle can be characterized on the basis of this behaviour.

Figure 9:
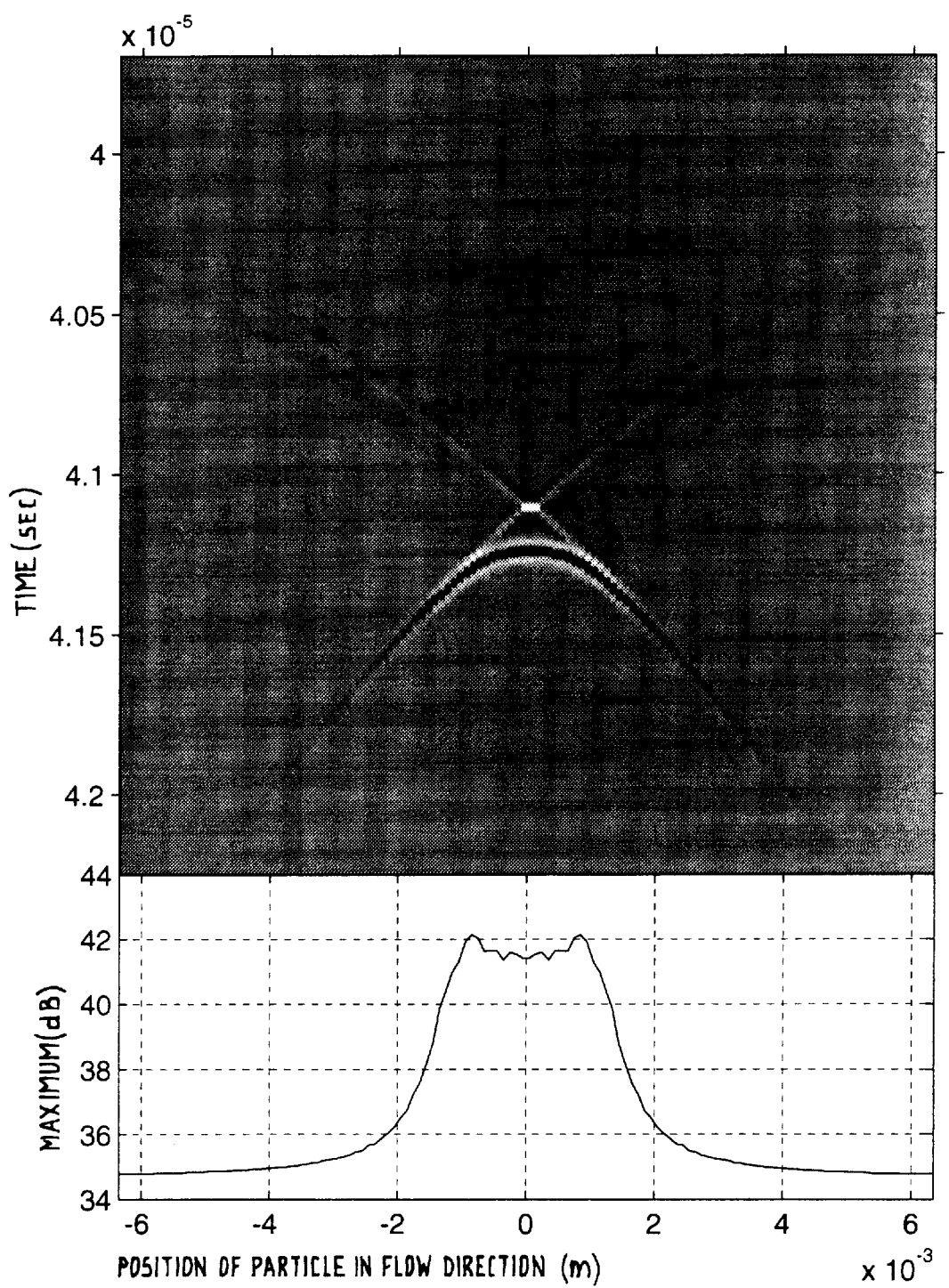
FIG. 9 shows successive recordings for a single spherical particle in a flowing suspension using the measurement set-up according to FIG. 3.
Figure 10:
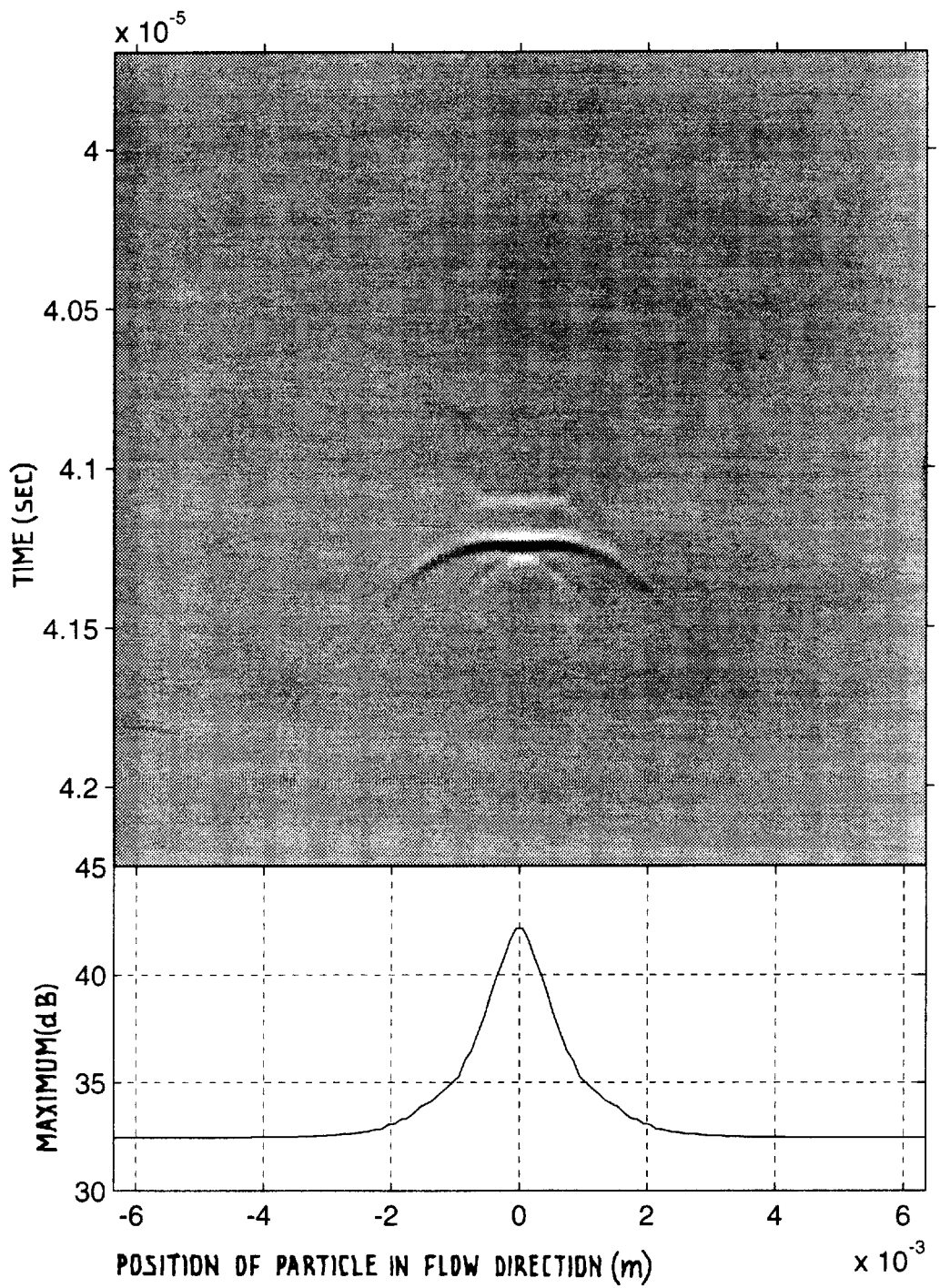
FIG. 10 shows successive recordings of a single elongated particle with a length of 1 mm in a flowing suspension using the measurement set-up according to FIG. 3.

FIG. 9 shows a succession of simulated recordings for a spherical particle which passes through the beam at a fixed distance beyond the focus. Simulated recordings for an elongated particle are given in FIG. 10. These Figures clearly illustrate the effect of the shape of the particle on the reflection behaviour as a function of the angle.

Figure 11:
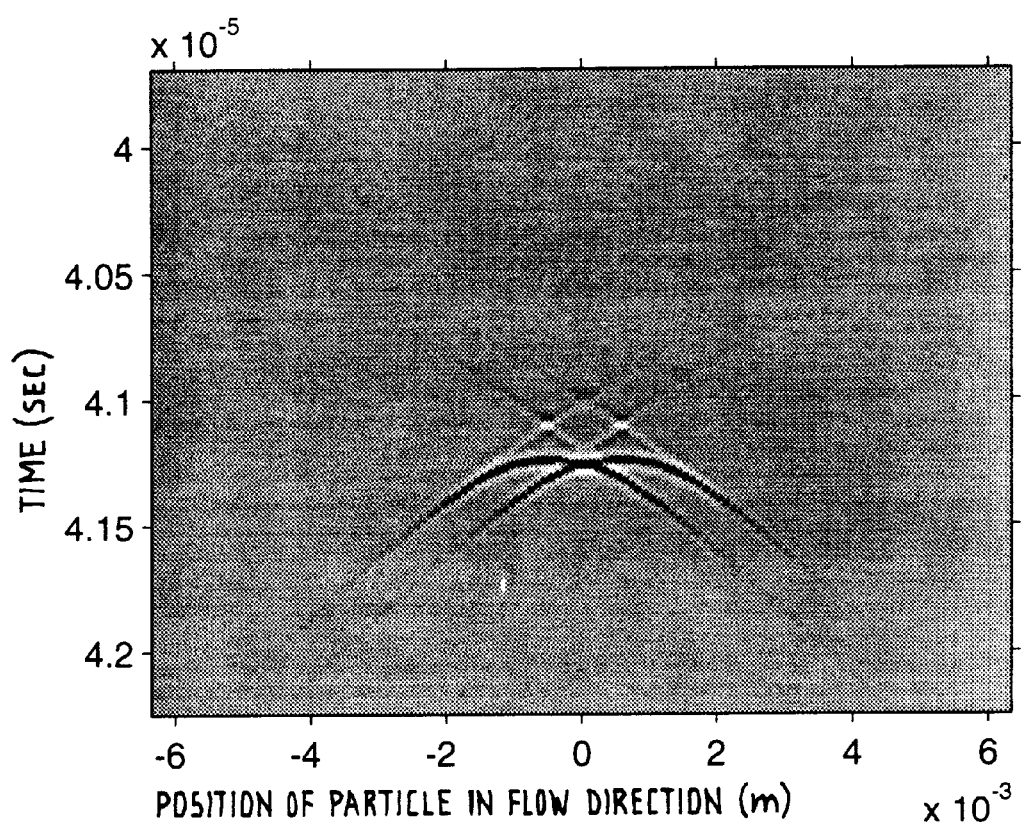
FIG. 11 shows a sequence of recordings for two particles 0.5 mm apart.

For this method, the larger the aperture of the beam from the transducer 23, the more clearly visible is the difference in angle-dependent behaviour between different types of particles. As a result, the measurement volume is dispensed with with this method because different particles located laterally alongside one another can be individually recognised in the succession of recordings. This is illustrated in FIG. 11, where two spherical particles pass through the beam just behind one another. Although the lateral distance (15 mm) between these particles is much smaller than the beam diameter, the reflections originating from the first particle can be separated from the reflections from the second particle in the succession of recordings. The most important characteristic of the last-mentioned embodiment is that the beam has a large aperture and that the time which elapses between two successive measurements is so short that each particle is exposed several times during its presence in the beam. As has been explained above, this can be achieved, for example, with the aid of a focused transducer. Theoretically, the use of a point source or a relatively small source (of the order of magnitude of the wave-length used) is also possible. It is only at high frequencies that this cannot be achieved in practice. Optionally, use can be made of a Radon transformation or a 2D Fourier transformation to the $k_x$-k domain in order to quantify the angle-dependent reflection behaviour of each recorded particle.

Following the characterisation of a particle on the basis of its angle-dependent behaviour, the cumulative count curve can be determined for each type of particle. For this purpose the maximum amplitude for the series of recordings originating from the particle concerned (this is the amplitude when the particle is located on the principal axis z of the beam 20) is taken as the amplitude per detected particle. This maximum amplitude can still vary for one type of particle because of variations in particle size and variations in the minimum lateral distance from the principal axis z at which the particle passes through the beam. A cumulative count curve similar to that illustrated above with reference to FIGS. 4, 5 and 6 will be found for each type of particle.

A possible application of the method described above is the measurement of thrombus particles in a blood stream. Patients who have a heart valve prosthesis have an increased risk of thrombosis because the artificial valve promotes the production of thrombus particles. Therefore, these patients have an increased risk of acute vascular occlusion as a result of too large a thrombus particle. This can lead, for example, to cerebral infarction.

Anticoagulants are administered to the patient to counteract thrombus formation. The risk of too high a dosage of these anticoagulants is the occurrence of haemorrhaging (for example cerebral haemorrhaging). Currently the dosage is determined on the basis of the coagulation measured on a blood sample. However, this is an unreliable method because the coagulation is dependent on many more factors than solely the concentration of thrombi. Moreover, a measurement of this type provides only a snapshot.

It is therefore desirable to have available a method with which the concentration of thrombi in the blood can be measured reliably. The measurement method described here is suitable for this purpose.

By using a transmission frequency of the sound waves which is relatively high for medical application, for example in the range of 10–40 MHz, preferably 20–30 MHz, it is possible to detect small particles present in the blood. The depth of penetration is still found to be sufficiently great at these frequencies. By making use of the high efficiency of, for example, a composite transducer and of sophisticated transmission and reception electronics, it is possible to achieve an adequate depth of penetration, so that an echo-acoustic recording of the blood can be made using a non-invasive technique. However, blood also contains other particles which will be detected by the ultrasonic reflection method, for example red blood cells.

It is known that red blood cells form elongated aggregates during a certain period of the heart cycle (end of diastolic), which aggregates align with the flow. See, for example, M. G. M. de Kroon: "Acoustic backscatter in arteries—Measurements and modelling of arterial wall and blood", thesis 1993, ISBN 90-9006182, Section III. It is possible to distinguish these long structures from thrombi, which are of a jagged shape (see: S. Chien: "Clinical Haemorheology", Martinus Nijhoff), on the basis of the angle-dependent behaviour.

After making this distinction, the concentration and size distribution of thrombi can be estimated on the basis of the cumulative count curves, as has been explained above.

We claim:

1. A method for the detection and identification of particles in a suspension, comprising the following steps:
   a. generation of acoustic signals having the form of a beam along a predetermined axis using an acoustic source;
   b. directing the acoustic signals at at least one measurement volume within the suspension, said at least one measurement volume having axial boundaries defined as boundaries in an axial direction of said axis, and lateral boundaries defined as boundaries in a direction lateral to said axis, said axial boundaries being defined with the aid of time windows;

c. reception of acoustic reflection signals produced by reflection of the acoustic signals by the particles in the at least one measurement volume;

d. conversion of the acoustic reflection signals into electrical reflection signals;

e. counting numbers of electrical reflection signals which have an amplitude value in excess of at least one predetermined threshold and conversion thereof into numbers of particles which are larger than a certain size; wherein the method also comprises the following steps:

f. composing at least one cumulative count curve showing for each amplitude value the number of electrical reflection signals having amplitude values in excess of said each amplitude value;

g. comparison of the at least one cumulative count curve with predetermined standard cumulative count curves and deduction of at least one feature selected from the group consisting of material properties, particle concentration, particle shapes, particle size and standard deviation thereof and particle size distribution;

the standard cumulative count curves being derived with at least the following steps:

derivation of a probability density function for plural amplitude values of the electrical reflection signals within the measurement volume as a function of a given particle shape, and particle size distribution thereof, and derivation of the standard cumulative count curves from the probability density function for the plural amplitude values.

2. A method according to claim 1, wherein derivation of the standard cumulative count curves also includes the step of:

definition of the lateral boundaries of the at least one measurement volume as being the boundaries beyond which amplitudes of the electrical reflection signals are smaller than a predetermined noise level.

3. A method according to claim 1, wherein the following equation is used for the probability density function for the amplitude values:

$$p(A) = \int g(A|D)\, h(D)\, dD$$

where:

g(A|D)=probability density function for measured amplitude A of an electrical reflection signal originating from an arbitrary particle having a diameter D;

h(D)=probability density function for particle diameter D, the equation being integrated between two predetermined limits for the particle diameter D.

4. A method according to claim 3, wherein, for detecting a particle in the measurement volume, a Gaussian amplitude profile of the acoustic signals in a first direction in the measurement volume lateral to said axis and a substantially negligible amplitude variation in the acoustic signals in a second direction in the measurement volume parallel to said axis are assumed for determination of g(A|D), resulting in the relation:

$$g(A|D) = \begin{bmatrix} \frac{1}{A} \frac{1}{\ln A_0(D) - \ln A_n} \end{bmatrix} \quad \text{if } A_n < A < A_0(D)$$
$$0 \quad \text{if } A > A_0(D) \wedge A < A_n$$

where $A_n$=noise level, $A_o$ is the amplitude which would be detected from said particle if said particle where located on the axis.

5. A method according to claim 1, wherein standard cumulative count curves are determined experimentally with the aid of suspensions containing particles of a pre-known shape, size and standard deviation of the size.

6. A method according to claim 1 where the particle concentration is calculated from the number of electrical reflection signals with amplitude values above a predetermined noise level.

7. A method according to claim 6, where the calculated particle concentration is corrected for the fact that smaller particles cannot be detected through the whole measurement volume, resulting in a true particle concentration.

8. A method according to claim 7, wherein, for detecting a particle in the measurement volume, a Gaussian amplitude profile of the acoustic signals in a first direction in the measurement volume lateral to said axis and a substantially negligible amplitude variation in the acoustic signals in a second direction in the measurement volume parallel to said axis are assumed for correcting said calculated particle concentration, resulting in the following relation for the true particle concentration C:

$$C = \frac{N(A > A_n)}{N_{tot} V_{meas}} \left[ \frac{1}{\xi} \int_D q_{true}(D) dD \right]$$

where:

A=measured amplitude of an electrical reflection signal $A_n$=noise level

N( . . . ) gives the number of measurements for which the condition given in brackets applies, $N_{tot}$ is the total number of measurements, $V_{meas}$ is the measurement volume, $\epsilon$ is a normalizing factor and $q_{true}$ is a true particle size distribution.

9. A method according to claim 1, wherein said beam is focussed in a focus and the measurement volume is chosen to be around the focus of the acoustic beam and to be so small that the likelihood of the presence of more than one particle in the measurement volume during a measurement is negligibly small.

10. A method according to claim 1, wherein in step a, the acoustic beam generated is a focussed beam and has such a large aperture, and the time which elapses between two successive measurements is so short, that each particle is exposed several times while passing through the beam and that, depending on the position of a particle lateral to said axis in the measurement volume, a varying angle-dependent reflection of the acoustic signals is produced;

prior to step f, one or more different types of particles present in the suspension are identified on the basis of a series of angle-dependent reflection signals received successively over time;

when composing the curve in step f, the maximum value of each amplitude value of said series of successive angle-dependent reflection signals, received over time, from a detected particle from the one or more types is taken as the amplitude of the electrical signals, which are produced after conversion of the acoustic reflection signals from said detected particle.

11. A method according to claim 10, wherein in step a, the focused acoustic beam with a predetermined focus is generated and in step b the focus remains outside the measurement volume.

12. A method according to claim 10, wherein an acoustic source having dimensions smaller than the wavelengths of the generated acoustic signals is used.

13. A method according to claim 1, wherein the acoustic signals comprise sound signals having a frequency of 10–40 MHz.

14. A method according to claim 13, wherein the acoustic signals comprise sound signals having a frequency of 20–30 MHz.

15. Equipment for the detection and identification of particles in a suspension, comprising:
   a. an acoustic source for the generation of acoustic signals;
   b. means for directing the acoustic signals at at least one measurement volume within the suspension, each measurement volume having axial boundaries defined as boundaries in an axial direction of said axis, and lateral boundaries defined as boundaries in a direction lateral to said axis, said axial boundaries being defined with the aid of time windows;
   c. means for receiving acoustic reflection signals produced by reflection of the acoustic signals by the particles in the at least one measurement volume;
   d. means for converting the acoustic reflection signals into electrical reflection signals;
   e. means for counting numbers of electrical reflection signals which have an amplitude value in excess of at least one predetermined threshold and for converting said counted numbers into numbers of particles which are larger than a certain size;
wherein the equipment also comprises:
   f. means for composing at least one cumulative count curve showing for each amplitude value the number of electrical reflection signals having amplitude values in excess of said each amplitude value;
   g. means for comparing the at least one cumulative count curve with predetermined standard cumulative count curves and for deducing at least one feature from a set of features comprising: material properties, particle concentration, particle shapes, particle size and standard deviation thereof and particle size distribution;
the standard cumulative count curves being derived with at least the following steps:
   derivation of a probability density function for plural amplitude values of the electrical reflection signals within the measurement volume as a function of a given particle shape, and particle size distribution thereof, and
   derivation of the standard cumulative count curves from a probability density function for the plural amplitude values.

16. Equipment according to claim 15, wherein
during operation, the acoustic source generates an acoustic beam which is focussed and has such a large aperture, and makes the time which elapses between two successive measurements so short, that each particle is exposed several times while passing through the beam and that, depending on the position of the particles lateral to said axis in the measurement volume, a different angle-dependent reflection of the acoustic signals is produced;
identification means are also present for identification of one or more different groups of particles present in the suspension on the basis of a series of successive angle-dependent reflection signals received over time;
the means for composing the at least one cumulative count curve compose the at least one cumulative count curve, the maximum value of the amplitude values of said series of successive angle-dependent reflection signals, received over time, from a detected particle being taken as the amplitude value of the electrical signals, which are produced after conversion of the acoustic reflection signals from said detected particle.

* * * * *